United States Patent
Bernardes

(10) Patent No.: US 7,856,135 B1
(45) Date of Patent: Dec. 21, 2010

(54) SYSTEM FOR ANALYZING OCULAR FUNDUS IMAGES

(75) Inventor: Rui Manuel Dias Cortesão dos Santos Bernardes, Coimbra (PT)

(73) Assignee: Aibili—Association for Innovation and Biomedical Research on Light and Image, Coimbra (PT)

( * ) Notice: Subject to any disclaimer, the term of this patent is extended or adjusted under 35 U.S.C. 154(b) by 0 days.

(21) Appl. No.: 12/629,661

(22) Filed: Dec. 2, 2009

(51) Int. Cl.
*G06K 9/00* (2006.01)
*G06K 9/32* (2006.01)

(52) U.S. Cl. ........................ 382/131; 382/300

(58) Field of Classification Search ......... 382/131–132, 382/300
See application file for complete search history.

(56) References Cited

U.S. PATENT DOCUMENTS

| | | | |
|---|---|---|---|
| 4,824,238 A * | 4/1989 | Feldman et al. ............. 351/206 |
| 4,833,625 A | 5/1989 | Fisher et al. | |
| 5,003,979 A * | 4/1991 | Merickel et al. ............ 600/410 |
| 5,233,517 A | 8/1993 | Jindra | |
| 6,104,828 A | 8/2000 | Shioiri | |
| 6,614,452 B1 * | 9/2003 | Cable ........................ 715/764 |
| 6,993,167 B1 | 1/2006 | Skladnev et al. | |
| 7,088,850 B2 * | 8/2006 | Wei et al. .................... 382/128 |
| 7,147,329 B2 | 12/2006 | Berger | |
| 7,327,390 B2 | 2/2008 | Gallagher | |
| 7,583,827 B2 | 9/2009 | Hansen et al. | |
| 7,593,559 B2 | 9/2009 | Toth et al. | |
| 7,599,542 B2 | 10/2009 | Brockway | |
| 2005/0094099 A1 | 5/2005 | Newman | |
| 2007/0002275 A1 | 1/2007 | Yan et al. | |
| 2007/0140542 A1* | 6/2007 | Spahn ....................... 382/132 |
| 2007/0160271 A1 | 7/2007 | Doi et al. | |
| 2007/0188705 A1 | 8/2007 | Tajima | |
| 2007/0258630 A1 | 11/2007 | Tobin | |
| 2007/0292037 A1 | 12/2007 | Allon | |
| 2008/0027314 A1 | 1/2008 | Miyazaki et al. | |

(Continued)

FOREIGN PATENT DOCUMENTS

JP 2009-022506 A 11/2009

(Continued)

OTHER PUBLICATIONS

Tobin, Kenneth W. et al., Using a Patient Image Archive to Diagnose Retinopathy, 30th Annual International Conference of the IEEE Engineering in Medicine and Biology Society, EMBS 2008, pp. 5441-5444, Aug. 20-25, 2008, Vancouver, Canada.

(Continued)

*Primary Examiner*—Bhavesh M Mehta
*Assistant Examiner*—Hadi Akhavannik
(74) *Attorney, Agent, or Firm*—SNR Denton US LLP

(57) ABSTRACT

An image analysis system provides for importing, normalizing and co-registering a plurality of ocular fundus images, or images obtained by their decomposition, analysis, processing, or synthesis. Differences between the image are determined and of those differences those that are meaningful (e.g., from a diagnostic point of view) are highlighted. Sequences of these differences, which reflect changes in the eye represented in the images, are synthesized so as to present a view of how the differences manifest over time. Structures of importance in the eye are overlapped so that the information may be presented in a meaningful fashion for diagnostic purposes.

3 Claims, 2 Drawing Sheets

U.S. PATENT DOCUMENTS

| | | |
|---|---|---|
| 2008/0107310 A1 | 5/2008 | Vilser |
| 2008/0312552 A1 | 12/2008 | Zhou et al. |
| 2009/0136100 A1 | 5/2009 | Shinohara |
| 2009/0270717 A1 | 10/2009 | Newman |

FOREIGN PATENT DOCUMENTS

| | | |
|---|---|---|
| WO | 9617545 A1 | 6/1996 |
| WO | 0051080 A1 | 8/2000 |
| WO | 2009124306 A1 | 10/2009 |
| WO | 2009126112 A1 | 10/2009 |
| WO | 2009129624 A1 | 10/2009 |

OTHER PUBLICATIONS

Lalonde, M. et al., RetsoftPlus: a tool for retinal image analysis, Proceedings 17th IEEE Symposium on Computer-Based Medical Systems, CBMS 2004, pp. 542-547, Jun. 24-25, 2004, Montreal, Canada.

Tsai, Chia-Ling et al., Automated Retinal Image Analysis over the Internet, IEEE Transactions on Information Technology in Biomedicine (TITB), vol. 12, issue 4, pp. 480-487, Jul. 2008 (manuscript dated Dec. 15, 2006).

Sakuma, S. et al., Image registration, color correction and change detection based on value of difference in sequential ocular fundus images, Systems and Computers in Japan, vol. 37, No. 11, pp. 100-112, Oct. 2006.

Sakuma, S. et al., Automated detection of changes in sequential color ocular fundus images, Proceedings of 1998 SPIE Image Processing Conference, vol. 3338, pp. 1377-1385, San Diego, CA, Feb. 23-27, 1998.

Carrott, D.T. et al., Opthalmologic image normalization using optical correlation, Proceedings of the 1997 SPIE Conference on Algorithms, Devices and Systems for optical Information processing, vol. 3159, pp. 2-13, San Diego, CA, Jul. 28-29, 1997.

Shin, D.S. et al., Fundus image analysis: Geometric and radiometric normalization, Proceedings of the 1999 SPIE Conference on Ophthalmic Technologies, vol. 3591, pp. 129-136, San Jose, CA, Jan. 23-25, 1999.

Narasimha-Iyer, H. et al., Integrated analysis of vascular and nonvascular changes from color retinal fundus image sequences, IEEE Transactions on Biomedical Engineering, vol. 54, No. 8, pp. 1436-1445, Aug. 2007.

Smith, R.T. et al., Interactive image analysis in age-related macular degeneration (AMD) and Stargardt disease (STGD), 42nd Asilomar Conference on Signals, Systems and Computers 2008, pp. 651-654, Pacific Grove, CA, Oct. 26-29, 2008.

Ryan, N. et al., Registration of digital retinal images using landmark correspondence by expectation maximization, Image and Vision Computing, vol. 22, No. 11, pp. 883-898, Sep. 20, 2004.

Myint, Shein Soe & Chutatape, O., GA based registration of temporal and multimodal ocular fundus image pairs, Proceedings of the SPIE Conference on Applications and Science of Neural Networks, Fuzzy Systems and Evolutionary Computation, vol. 4787, pp. 107-113, Seattle, WA, Jul. 9-10, 2002.

Narasimha-Iyer, H. et al., Robust detection and classification of longitudinal changes in color retinal fundus images for monitoring diabetic retinopathy, IEEE Transactions on Biomedical Engineering, vol. 53, No. 6, pp. 1084-1098, Jun. 2006.

Bernardes, R, et al., Computer-Assisted Microaneurysm Turnover in the Early Stages of Diabetic Retinopathy, Opthalmologicia 2009, vol. 223, No. 5, pp. 284-291, 2009.

\* cited by examiner

200

SYSTEM FOR ANALYZING OCULAR FUNDUS IMAGES

FIELD OF THE INVENTION

The present invention is directed to a system for image analysis, and in particular, to the analysis of digital ocular fundus images.

BACKGROUND

Diagnosing pathologies of the eye often involves examination of ocular fundus images. For example, in US PGPUB 2007/0002275, Yan et al. describe a method and system for the automatic detection of microaneursms in such images. More generally, these images can be used to diagnose a variety of conditions, for example from a review of differences in such images taken over a period of time.

Automated detection of differences between ocular fundus images requires an understanding of purportedly normal conditions and, inasmuch as it is difficult to determine such conditions, often produces less than satisfactory results. At the same time, manual screening of such images is a time-consuming and operator-dependent process. That is, the results of manual screening are often solely depend on the skill of the observer who is expected to make meaningful comparisons of images captured at different times in different conditions. Inevitably, some misdiagnoses are made.

SUMMARY OF THE INVENTION

An image processing system is provided. In one embodiment, the system includes a module for importing ocular fundus images, which images may have been captured at a variety of different times. Preferably, where they are to be used for diagnostic purposes, the images are sequenced in time from earliest to latest. The system also includes a processing module configured to normalize/correct the images before and further processing. Optionally, additional information may be associated with the images to permit fine resolution corrections to be made bases on patient state, image capture parameters or conditions, etc. The normalized/corrected images are then co-registered so as to permit differences between the images to be determined. The differences between any two of images, or images obtained by their decomposition or analysis/processing/synthesis, may be determined by subtraction or other comparison. Importantly, it is the important (e.g., from a diagnostic standpoint) differences which are determined.

In order to present the difference information in a meaningful fashion, the sequences of differences are synthesized with reference to a common baseline and then assembled in such a way to highlight the important differences with respect to structural features of the eye and how the differences have manifest over time. This permits users to observe how the images have changed over time.

BRIEF DESCRIPTION OF THE DRAWINGS

The present invention is illustrated by way of example, and not limitation, in the figures of the accompanying drawings, in which.

DETAILED DESCRIPTION

Figure 1:
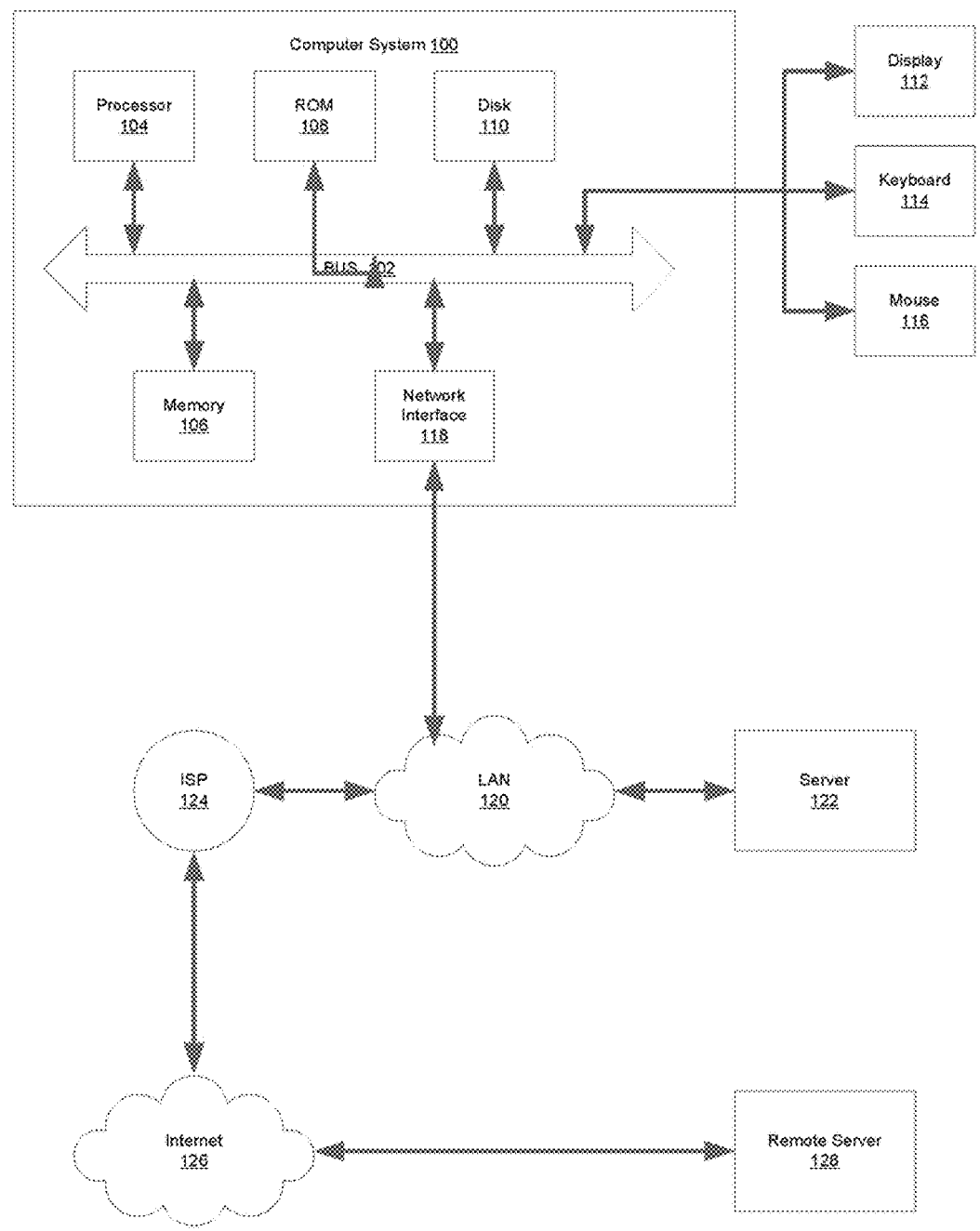
FIG. 1 illustrates an example of a computer system in which embodiments of the present invention may be instantiated.

Described herein is a system for image analysis, in particular, analysis of digital ocular fundus images. In brief, the present system provides for importing and normalizing a plurality of ocular fundus images, and coregistering the normalized images for further analysis, i.e., detecting differences between any two of the normalized images, or images obtained by their decomposition or analysis/processing/synthesis. Once detected, the differences between pairs (or more) of images are compared to highlight those differences which are significant (e.g., for diagnostic purposes), and sequences of changes in the images (which are usually collected over a period of time) synthesized so as to present a view of how the differences manifest over time. Optionally, additional information regarding the images and/how how they were captured, can be used to further refine the analysis. The various differences between images can be encoded and the various changes overlapped so that the information is presented in a meaningful fashion for diagnostic purposes. This can be done using overlays which highlight structurally significant features of the eye so that the differences in the images are provided with reference to those features.

Various embodiments of the present invention may be implemented with the aid of computer-implemented processes or methods (i.e., computer programs or routines) that may be rendered in any computer language including, without limitation, C#, C/C++, assembly language, markup languages, and the like, as well as object-oriented environments such as the Common Object Request Broker Architecture (CORBA), Java™ and the like. In general, however, all of the aforementioned terms as used herein are meant to encompass any series of logical steps performed in a sequence to accomplish a given purpose.

In view of the above, it should be appreciated that some portions of the detailed description that follows are presented in terms of algorithms and symbolic representations of operations on data within a computer system memory or other data store. These algorithmic descriptions and representations are the means used by those skilled in the computer science arts to most effectively convey the substance of their work to others skilled in the art. An algorithm is here, and generally, conceived to be a self-consistent sequence of steps leading to a desired result. The steps are those requiring manipulations of representations physical items, such as performing enhancements or other operations involving fundus images of the eye. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like. It should be borne in mind, however, that all of these and similar terms are to be associated with the appropriate physical quantities and are merely convenient labels applied to these quantities. Unless specifically stated otherwise, it will be appreciated that throughout the description of the present invention, use of terms such as "processing", "computing", "calculating", "determining", "displaying" or the like, refer to the action and processes of a computer system or systems, or similar electronic computing device, that manipulates and transforms data represented as physical (electronic) quantities within its registers and memories into other data similarly represented as physical quantities within its memories or registers or other such information storage, transmission or display devices.

The present invention can be implemented with an apparatus to perform the operations described herein. This apparatus may be specially constructed for the required purposes, or it may comprise a computer system that has been selectively activated or configured by a computer program executed by the computer system. Such a computer program may be stored in/on a computer-readable storage medium, such as, but not limited to, any type of disk including floppy disks, optical disks, CD-ROMs, and magnetic-optical disks, read-only memories (ROMs), random access memories (RAMs), electrically programmable ROMs (EPROMs), electrically erasable and programmable ROMs (EEPROMs), magnetic or optical cards, or any type of tangible media suitable for storing electronic instructions, and each readable by a computer system processor or the like.

The algorithms and processes presented herein are not inherently related to any particular computer or other apparatus. Various general-purpose systems (which become special purpose systems once appropriately programmed) may be used with programs in accordance with the teachings herein, or it may prove convenient to construct more specialized apparatus to perform the required methods. For example, any of the methods according to the present invention can be implemented in hard-wired circuitry, by programming a general-purpose processor or by any combination of hardware and software. One of ordinary skill in the art will immediately appreciate that the invention can be practiced with computer system configurations other than those described below, including hand-held/mobile devices, multiprocessor systems, microprocessor-based and/or digital signal processor-based devices, and the like. The invention can also be practiced in distributed computing environments where tasks are performed by remote processing devices that are linked through a communications network. The required structure for a variety of these systems will appear from the description below.

Referring now to FIG. 1, an exemplary computer system 100 upon which an embodiment of the invention may be implemented is shown. Computer system 100 includes a bus 102 or other communication mechanism for communicating information, and a processor 104 coupled with the bus 102 for executing the computer software which is an embodiment of the invention and for processing information (such as digital ocular fundus images) in accordance therewith. Computer system 100 also includes a main memory 106, such as a RAM or other dynamic storage device, coupled to the bus 102 for storing information and instructions to be executed by processor 104. Main memory 106 also may be used for storing temporary variables or other intermediate information during execution of instructions to be executed by processor 104. Computer system 100 further includes a ROM or other static storage device 108 coupled to the bus 102 for storing static information and instructions for the processor 104. A storage device 110, such as a hard drive or solid state storage device, is provided and coupled to the bus 102 for storing information and instructions.

Computer system 100 may be coupled via the bus 102 to a display 112, such as a liquid crystal display (LCD) or other display device, for displaying information to a user. An input device 114, including alphanumeric and other keys, is coupled to the bus 102 for communicating information and command selections to the processor 104. Another type of user input device is cursor control 116, such as a mouse, a trackball, or cursor direction keys for communicating direction information and command selections to processor 104 and for controlling cursor movement on the display 112. This input device typically has two degrees of freedom in two axes, a first axis (e.g., x) and a second axis (e.g., y) allowing the device to specify positions in a plane.

In embodiments of the invention which are instantiated as computer programs (i.e., computer-readable/executable instructions stored on a computer-readable medium), such programs are typically stored on storage device 110 and at run time are loaded into memory 106. Processor 104 then executes sequences of the instructions contained in main memory 106 to perform the steps described below. In alternative embodiments, dedicated circuitry or modules (or, in some cases, firmware-enabled application specific integrated circuits or specialized processors) may be used in place of or in combination with computer software instructions to implement the invention.

Computer system 100 also includes a communication interface 118 coupled to the bus 102. Communication interface 108 provides a two-way data communications between computer system 100 and other devices, for example via a local area network (LAN) 120. These communications may take place over wired and/or wireless communication links. In any such implementation, communication interface 118 sends and receives electrical, electromagnetic or optical signals which carry digital data streams representing various types of information. For example, two or more computer systems 100 may be networked together in a conventional manner with each using the communication interface 118.

Network 120 may also provides communication to one or more networks and other devices associated with those networks. For example, network 120 may provide a connection to a server 122 (which may store images for processing) and/or to data equipment operated by an Internet Service Provider (ISP) 124. ISP 124 in turn provides data communication services through the world wide communication network now commonly referred to as the "Internet" 126, through which remote computer systems such as remote server 128 may be accessed.

Figure 2:
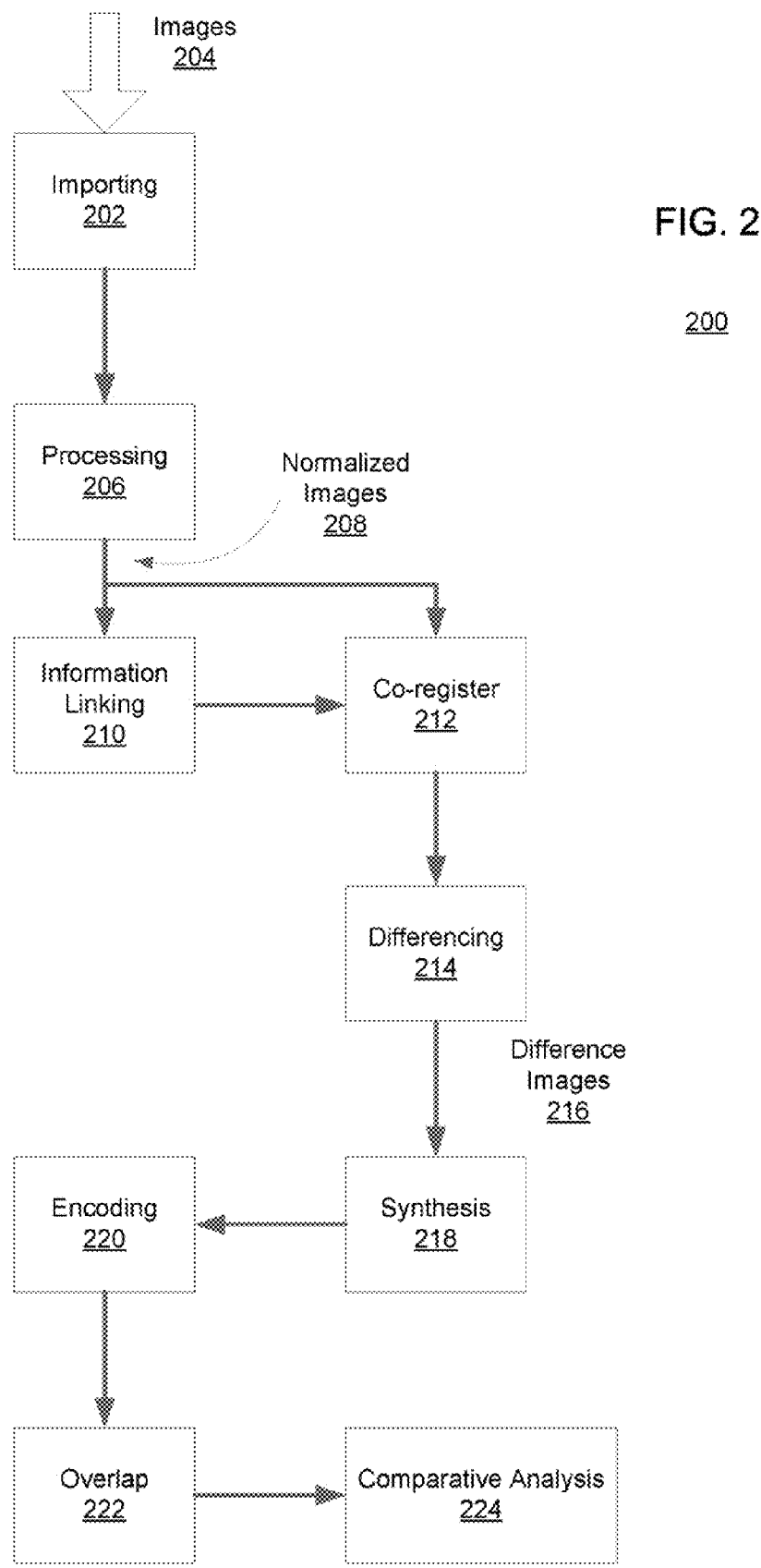
FIG. 2 illustrates an example of the modules which comprise an image processing system according to an embodiment of the present invention.

Now referring to FIG. 2, a system 200 which is an embodiment of the present invention is illustrated. System 200 includes several modules, each of which may be implemented as part of a common computer program to be executed by a computer system such as computer system 100. Alternatively, the modules may be implemented separately, with outputs from a preceding module being provided as inputs to a succeeding module. In other instances, some or all of the modules may be implemented in hardware, for example as application specific integrated circuits or programmable logic devices under firmware control. When implemented in software, various ones of the modules may be stored locally at computer system 100 (e.g., on storage device 110 to be loaded into memory 106 when executing), and/or at server 122 and/or remote server 128 (e.g., to be downloaded to memory 106 for execution by processor 104).

Module 202 is for importing ocular fundus images 204. This may be done manually, for example by a user of computer system 100 selectively uploading images, or automatically, for example by computer system 100 directly from equipment used to capture the images or from a data store, such as server 122 and/or remote server 128 (e.g., where the images may be stored in a database). The images can be imported by any convenient means, in any convenient format. Usually, the images will be sequenced in time, for example where the images are those of a single patient seen by a diagnostician (e.g., an ophthalmologist or optometrist) over a period of several years. In such instances, the images are preferably uploaded in a sequence from earliest to latest (i.e., older ones of images 204 should precede newer ones), or the images are tagged so that system 200 can readily identify the sequence in which the images 204 were taken. When imported into system 200, the images may be temporarily stored in memory (e.g., memory 106) while they undergo the processing discussed below. Images may be imported in bulk (if sufficient storage resources are available), or they may be imported sequentially, with each imported image undergoing processing before the processed version of the image is stored (e.g., in local storage on storage device 110 or in a network accessible storage location), and a subsequent, pre-processed image then being imported.

The images, once imported, are then provided to a processing module 206. Processing module 206 may be implemented using a suitable programmed computer system 100 and acts to normalize the imported images. Because images 204 are taken at different times, possibly using different equipment, and almost certainly under differing conditions such as patient state (e.g., dilated, not dilated, the time between dilation to when the image is captured, orientation of the patient vis-a-vis the image capture equipment, etc.), illumination (including lighting conditions in the room where the image capture equipment is operating and non-uniform illumination of the eye by the various image capture systems), etc. The normalizing process in performed automatically, image by image, to produce normalized images 208. Importantly, normalizing does not require a priori knowledge of where or how the image was captured.

Many techniques are available for normalizing the images. For example, as explained by Yan, the so-called shading effect may result in varying image intensity in the background. The shading effect is very undesirable, but can be corrected by first estimating a background image and then subtracting the estimated background image from the original (e.g., by low pass filtering the original image). Step effects introduced as a result of shading correction may be reduced by smoothing the shade-corrected image. The precise methods used to perform such normalizing at not critical to the present invention. What is important is that normalized images 208 are available for subsequent processing by system 200. The normalized images may be stored, locally or remotely, prior to further operations being performed.

The normalized images will be subjected to further processing, however, in some instances additional information will be linked to each normalized image 208 using an information linking module 210. Module 210 is optional, but when present it is used to associate information regarding the patient, the image capture equipment used to capture an associated image (e.g., field of view, illumination parameters, etc.), the procedure used to capture an associated image, image acquisition conditions, or any combination of the foregoing. While such information is not needed to further process the images, when available this information can be beneficial and can allow for fine tuning of the image preprocessing.

Module 210 may operate manually, e.g., with a user entering the various information concerning the images, or automatically, with system 200 reading the information from one or more files of meta information concerning the images and associating same with the normalized versions thereof. By having this extra information available, system 200 is able to further correct the images to account for the unique circumstances of patient and image capture conditions. For example, the information may be used to influence weights used by the normalizing algorithms.

Whether or not the normalized images are refined using the additional information, the normalized images are provided to a co-registration module 212. As the name implies, co-registration module 212 is configured for overlaying pairs or multiple ones of the normalized images over each other with the correct orientation and geometry so that corresponding internal features in those images align. Co-registration allows the comparison of images with one another described below. Before images can be compared to determine differences therebetween, the images must be aligned so that the comparisons are meaningful.

Once the images have been co-registered with one another, they can be compared with one another to determine differences between the images. This comparison is performed by differencing module 214. Usually, differencing is done between two images taken sequentially in time, however, in some cases, it may be useful to take differences over images separated by multiple intervening images. For example, where images separated by relatively short periods of time are used, it may be beneficial to take differences between two (or more) of such images that are separated by relatively long periods of time. Further, in some cases, the images subjected to the differencing may be images obtained by the decomposition or analysis, processing, or synthesizing of the normalized images.

The image differencing process may make use of statistical processes to compare two, or more, normalized images with one another and determine the level of change therebetween. Differences may be computed at a pixel-by-pixel, or region of pixels, level. In general, two images are compared with one another by subtracting one from the other, and the result applied to a low pass filter to generate a difference image 216. In some cases, where color images are present, prior to differencing the images they are converted to gray scale images. This conversion is, generally, a non-linear process that makes use of principal component analysis or another method.

The difference images are provided to synthesis module 218, which is configured to synthesize a sequence of changes, optionally linked to a time reference, between the images, either image-by-image or with reference to a common, baseline image. The selection of images for this synthesis process may be either manual, by a user, or automatic.

It should be appreciated that when dealing with differences among images taken over a long time span (e.g., images captured every 6 months over a 10 year period) there will likely exist a great many differences between individual ones of the images. But producing results that reflect a significant number of differences, when in fact many of those images may not be meaningful, is not helpful to diagnosticians. Instead, system 200 may be configured to provide information concerning the most important changes or most important locations of images in which differences are detected. Thus, in one embodiment, system 200 is configured to compare each image to a baseline reference and assemble the difference data in such a way as to highlight important changes and how the associated differences in the images have manifest over time.

The output of the synthesis module 218 is provided to an encoder 220. Encoder 220 is a module configured to encode a sequence of changes in a visible and/or numeric form. Such encoding allows for defining of the changes in the images, recoding when the changes became visible, how the associated images deviate from the baseline, and how the changes have varied over time, etc. When represented in a convenient display format, the differences may be overlaid in different colors so a user can observe how the changes have manifest over time and what area(s) of the eye is (arc) affected. The overlapping function may be provided by a separate module 222 or may be integrated with the encoding module. In any event, such overlapping allows for a presentation of the image differences in a way that is meaningful with respect to the eye depicted in the images. The overlap may consist of a matrix reference that highlights features of the eye (e.g., the optic disc, the fovea, or any combination of these) as references. By allowing for the images differences to be displayed relative to the eye structures, the user is afforded an opportunity to see how the differences compare to the structure of the eye, making diagnoses of diseases easier.

Finally, and optionally, system 200 may include a comparative analysis module 224, which is configured to compare the sequences of differences on their relative locations on the eye fundus and/or size. This provides a "time lapse" representation of the changes as they manifest in the different images and with reference to the structures of the eye.

Thus, a system for image analysis, and in particular the analysis of digital ocular fundus images, has been described. While previous automated systems that make use of such images have been designed for automated diagnosis, e.g., to detect lesions such as microaneurysms, and so are unnecessarily complicated because such systems require a detailed understanding of purportedly "normal" conditions for such an image, the present system is designed identify and display those differences between images which are meaningful for diagnostic purposes, allowing diagnosticians to make informed diagnoses. Of course, the forgoing discussion of certain illustrated embodiments of the invention were not intended to place limits thereon. The invention should only be measured in terms of the claims, which now follow.

What is claimed is:

1. An image processing system, comprising:
   a module for importing a plurality of ocular fundus images;
   a module for receiving imported ones of the ocular fundus images and normalizing the ocular fundus images to produce normalized images;
   a module for coregistering the normalized images to produce normalized, co-registered images;
   a module for detecting differences between any two of the normalized, co-registered images;
   one or more modules configured to determine significant ones of the differences between the normalized, co-registered images and present only the significant ones of the differences in time sequence with an overlay of structural features of an eye which the images represent.

2. The image processing system of claim 1, wherein the one or more modules are further configured to synthesize sequences of changes in the images so as to present a view of the differences between the normalized, co-registered images over time.

3. The system of claim 1, further comprising a module to refine the normalized images prior to co-registration using information regarding the images and how they were captured.

* * * * *